Figure 1:
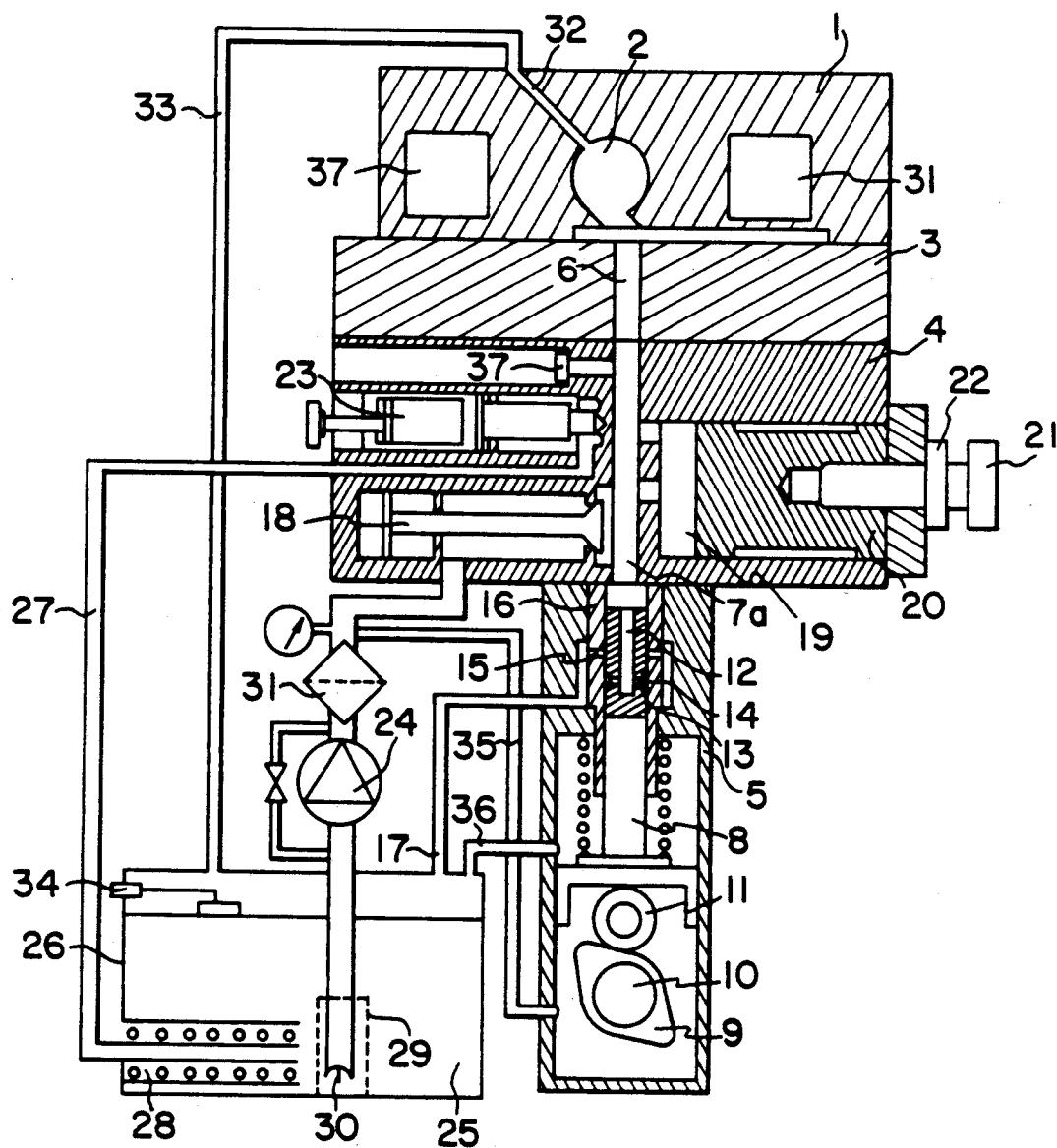

United States Patent [19]

Cofflard et al.

[11] Patent Number: 5,054,314
[45] Date of Patent: Oct. 8, 1991

[54] MECHANICAL FATIGUE TEST BENCH FOR ENGINE CYLINDER HEADS

[75] Inventors: Daniel Cofflard, Mouy; Maurice Bouvier, Villette d'Anton; Bernard Engler, Andresy, all of France

[73] Assignee: Montupet, Levallois-Perret, France

[21] Appl. No.: 573,777

[22] Filed: Aug. 28, 1990

[30] Foreign Application Priority Data

Aug. 29, 1989 [FR] France ................. 89 11521

[51] Int. Cl.⁵ .......................................... G01M 19/00
[52] U.S. Cl. .................................................. 73/118.1
[58] Field of Search ..................... 73/118.1, 807, 49.7

[56] References Cited
U.S. PATENT DOCUMENTS 3,690,162 9/1972 Stecher ........................... 73/49.7 X Primary Examiner—Jerry W. Myracle
Attorney, Agent, or Firm—Dennison, Meserole, Pollock & Scheiner

[57] ABSTRACT

This invention relates to a fatigue test bench for engine cylinder heads, particularly for motor vehicles. This bench comprises as main elements: a device for fixing the test cylinder head on an intermediate connecting member, connecting it to the means of establishing hydraulic pressure in the combustion chambers and in the circulating of the heat bearing fluids; a pressure generating device which simulates as faithfully as possible and in a reproducible manner the pressure cycle as a function of time in the combustion chambers; and a system of circulating heat bearing fluids through the water chambers of the cylinder head with two differnt circuits, one at ambient temperature and the other at a higher temperature used alternately by means of a regulable timing device which controls the operation of one or other of the circuits. The apparatus according to the invention makes it possible in a limited time, generally less than half the time required for tests on an engine bench: for a given type of cylinder head, to define the most suitable alloy or alloys; to develop new alloy compositions which are more suitable for the increasingly more severe demands encountered in the field of motor vehicle cylinder heads; to rapidly test new forms of cylinder heads; and to draw up comparative data of resistance to mechanical fatigue.

11 Claims, 4 Drawing Sheets

MECHANICAL FATIGUE TEST BENCH FOR ENGINE CYLINDER HEADS

The invention relates to a mechanical fatigue test bench for the cylinder heads of internal combustion engines, particularly those of motor vehicles.

The race for power and efficiency in the development of motor car engines means that the cylinder heads are subjected to increasingly more severe thermal and mechanical stresses. These stresses give rise to two types of breakdown in the cylinder head:
the first, of thermal origin, in the form of cracks in the combustion chamber
the second, of mechanical origin, in the form of cracks in the water chamber.

This second problem is at present resolved only by empirical modifications of shape of the cylinder head and of the composition of the alloy from which the cylinder head is produced, known by experience to be the most appropriate for withstanding stresses. The efficiency of modifications of form have to be checked on an engine test bench, a phase which it is hard to implement, expensive and requiring considerable time.

Therefore, there has been a need for an installation where just the cylinder head is tested quickly and in a reproducible manner.

The test bench according to the invention answers this problem.

Therefore, the bench comprises the following main elements:
a mechanical apparatus which makes it possible to fix the cylinder head being examined by a connecting part to the hydraulic equipment for pressuring the combustion chambers and for circulating the heat bearing fluid(s) through the water chambers
a pressure generating apparatus simulating as faithfully as possible the pressure cycle as a function of the time in the combustion chambers in a reproducible manner
a system for circulating heat bearing fluid through the water chambers with two different circuits, one at ambient temperature, the other at a higher temperature (which may be as high as 180°, for example) and which can be used alternately according to a programmed cycle.

To be more exact, the cylinder head being examined is fixed in conventional manner on a parallelepiped connecting member machined on one of its faces to the design of the cylinder head being examined (distance between centres of cylinders, inlet and outlet of circulating water, housing of fixing screws, etc.) and on its other faces the design of the hydraulic base unit and the distribution of heat bearing fluids. Fixing is carried out by screws and sealing-tightness is guaranteed by a conventional cylinder head gasket as on a conventional engine. It should be noted that the cylinder head is provided with its valves, all in the closed position.

The hydraulic base unit comprises a flat surface which matches the connecting member and a hydraulic apparatus for generating pressure (an injection pump).

Mounting of the connecting member on the hydraulic assembly is generally carried out by screws and sealing-tightness is obtained by O-rings. The hydraulic arrangement essentially comprises:
a supply reservoir provided with a level sensor
a supply pump
an inlet valve into the injection pump
injection pumps each of which is operated by a cam which decides the piston stroke of the pump
valves for regulating the maximum relative pressure between 2 and 20 MPa and the pressure gradient in a downwards direction
monitoring chambers of a volume which is variable but adjustable prior to test, to monitor the ascending pressure gradient between 5 and 10 MPa/ms approx.
a discharge device into each injection piston to improve expansion during the descending pressure phase
a compression fluid, usually oil.

It is supplemented by secondary devices such as:
a leakage orifice at the upper part of the cylinder head making it possible to drain off the initial air; this drain circuit is disposed in the original injector (.a calibrated diameter of 0.3 mm). It remains constantly open and there is therefore a permanent and slight leakage flow.
a heat exchanger which makes it possible to cool the compression fluid
a pressure sensor which makes it possible to monitor the variation in pressure as a function of the time.

The operating cams of the injection pumps (there are as many as there are cylinders in the engine) are symmetrical in relation to their axis and are offset by 45° in order to reproduce the conventional ignition sequence of the cylinders (for example, 1, 3, 4, 2 for a 4-cylinders engine).

The distribution of heat bearing fluids comprises two circuits constituted:
by two reservoirs of heat bearing fluids, one at ambient temperature, the other provided with heating and temperature regulating means
circulating pumps
a distribution device which makes it possible to connect the connecting member and the cylinder head to one or other of the circuits
pipes for return to the reservoir.

This apparatus is supplemented by bottom valves and strainers in the tanks, a heat exchanger in the "cold" tank, calibrated discharge valves which are provided as a safety measure.

The distribution apparatus consists, for example, of diaphragm valves which are themselves operated by programmable electrically operated valves. The cycle, the duration of which can be adjusted on each of the circuits, is greater than or equal to 3 minutes (which corresponds substantially to the time it takes to establish a thermal balance in the test cylinder head).

Figure 2:
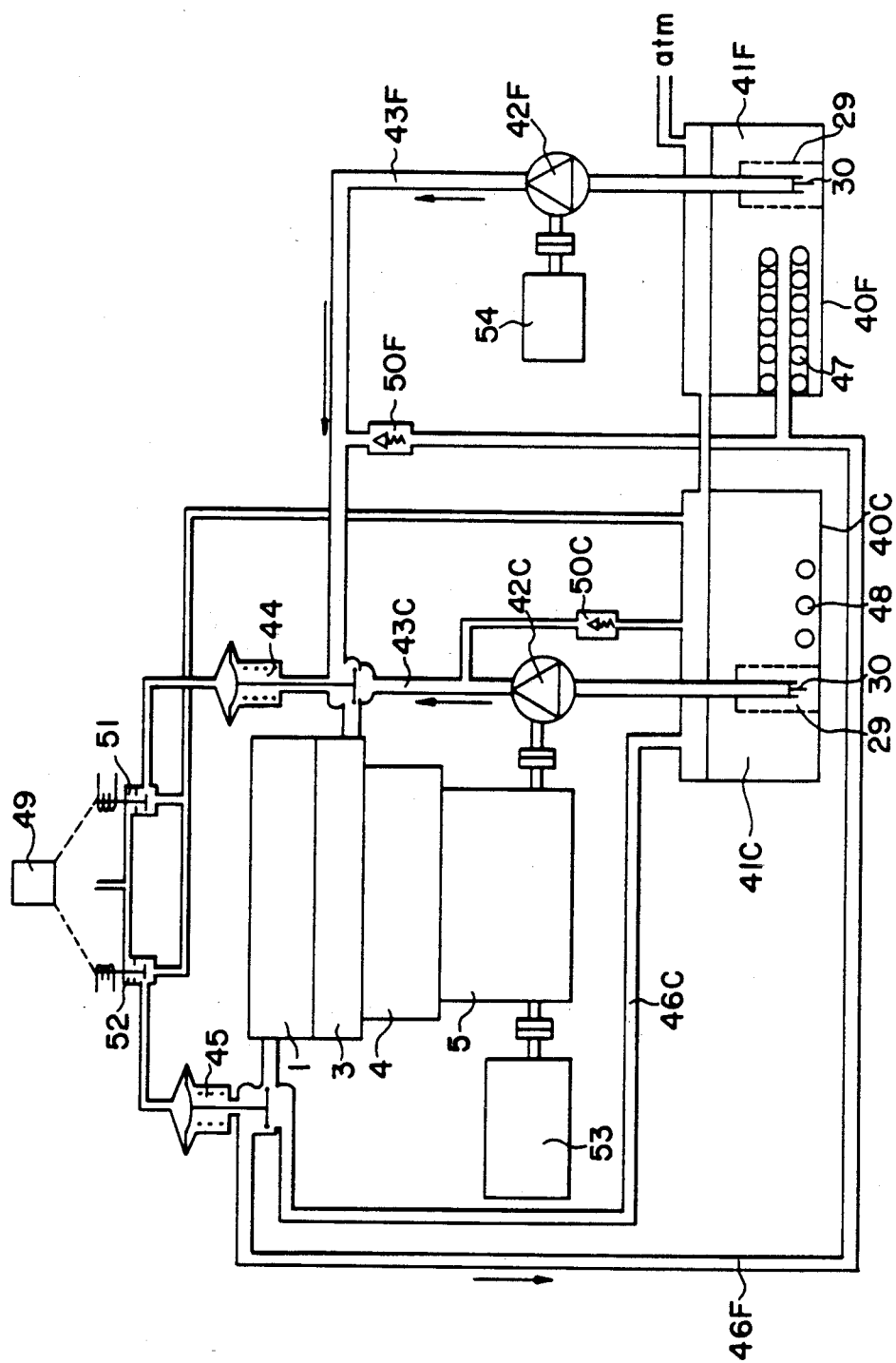
Figure 3:
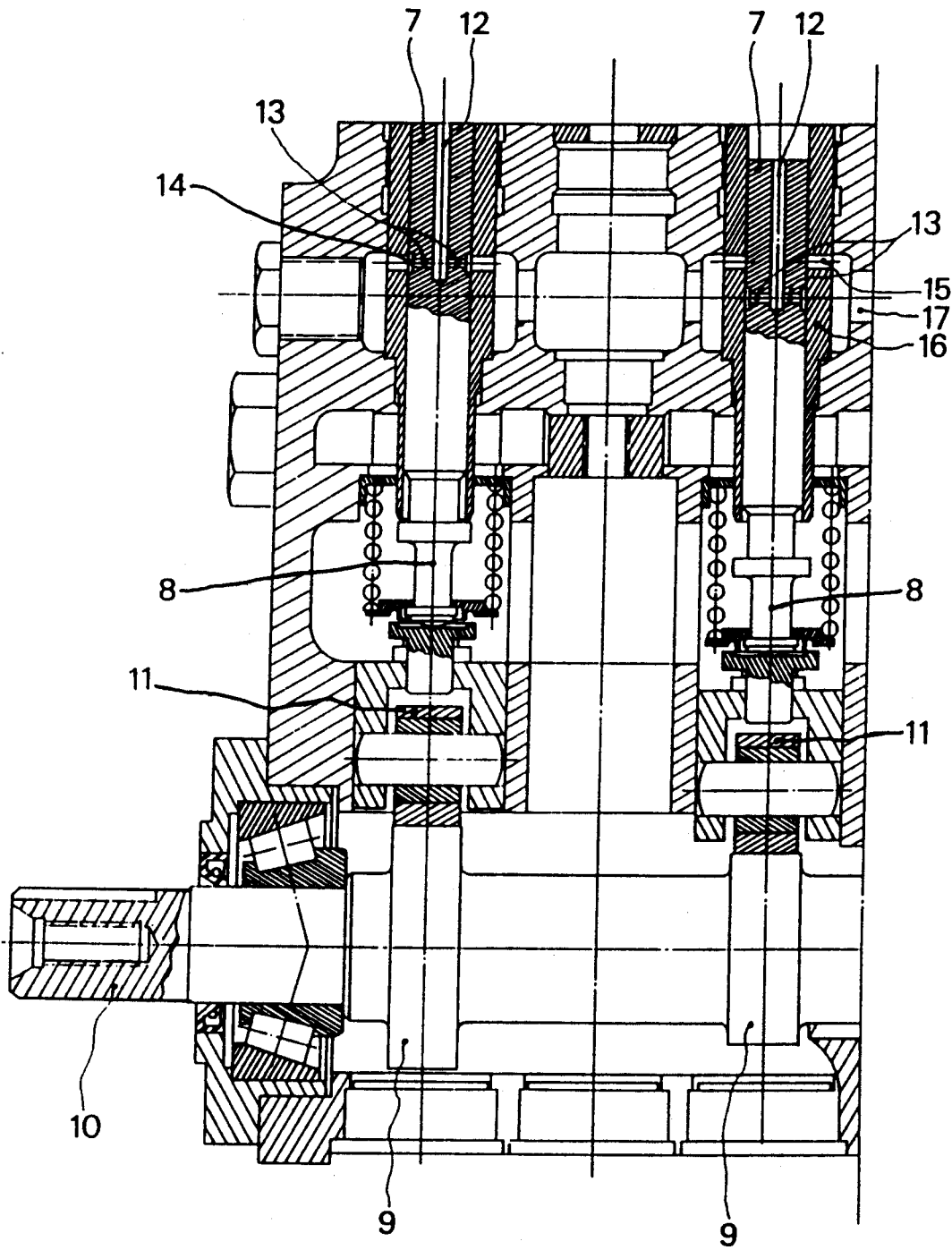
Figure 4:
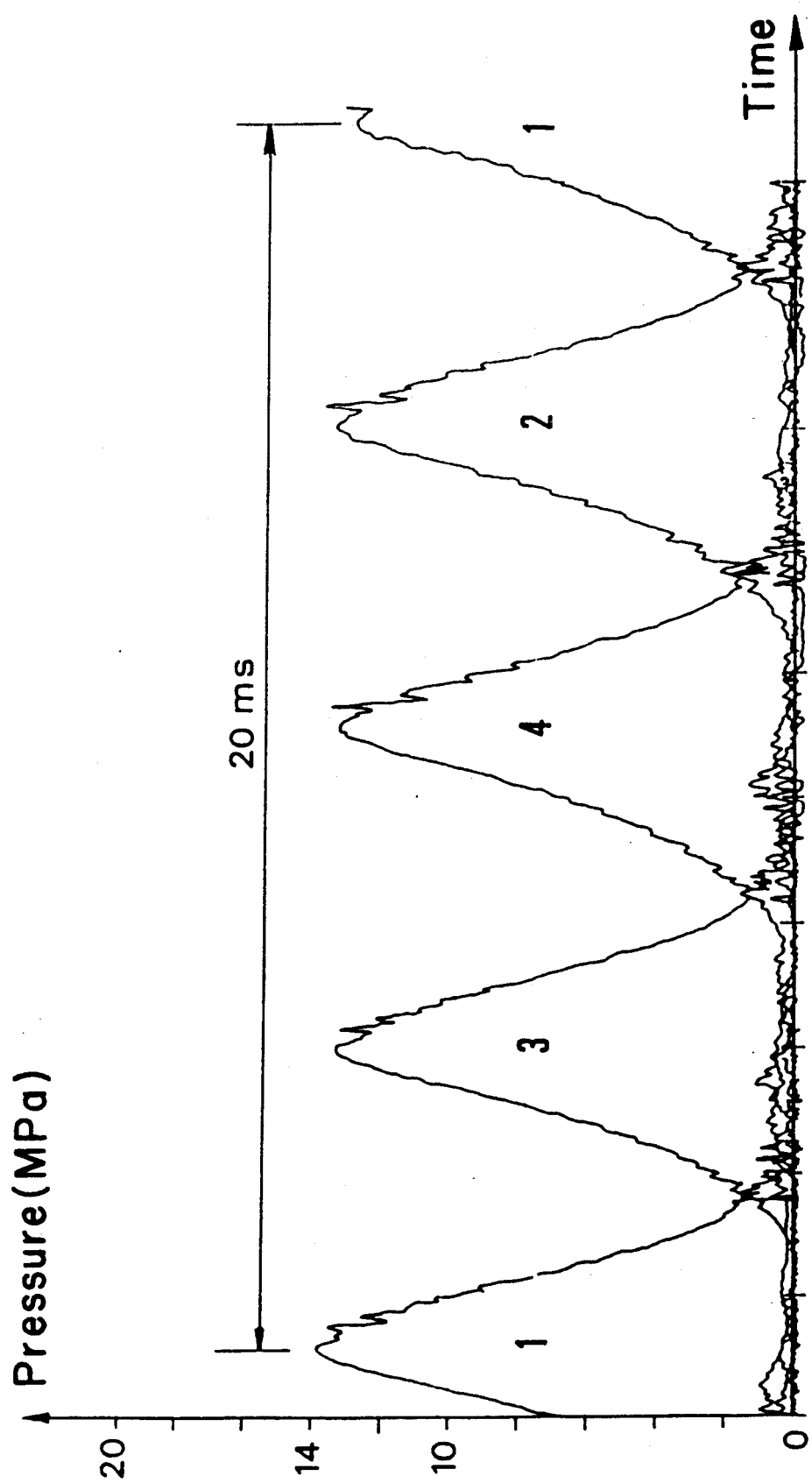

The invention will be more clearly understood from the following description which is illustrated by FIGS. 1 to 4, in which:
FIG. 1 diagrammatically shows a cross-section through the apparatus;
FIG. 2 diagrammatically shows the circuits of the heat bearing fluids;
FIG. 3 represents a cross-section through two injection pumps with the piston in the raised position for one (on the left) and in the low position for the other (on the right);
FIG. 4 shows by way of indication the development of pressure as a function of the time in each of the combustion chambers 1, 2, 3, 4.

The cylinder head 1 being tested, in which there is diagrammatically shown a combustion chamber 2 the base of which is fixed on the connecting member 3, sealing-tightness being provided by a cylinder head gasket (not shown).

The connecting member 3 has, provided in it, passages 6 which establish a connection with the injection pumps 5 through the hydraulic base unit 4, in which there are likewise passages 7a.

Each injection pump comprises a piston 8 operated by a roller 11 through a symmetrical cam 9 mounted on an engine shaft 10.

The piston head 7 comprises a central bore 12 connected by four ports 13 to a lateral groove 14. For the high position of the piston, this corresponds to apertures 15 in the liner 16 and the return circuit 17.

The hydraulic unit 4 comprises an inlet valve 18 for compression fluid 25, a chamber 19 the volume of which can be adjusted by means of a piston 20 of suitable length, a screw 21 and a lock nut 22.

It likewise comprises a pressure limiting valve 23 regulable between 2 and 20 MPa, of the bistable type (its closure pressure being very much less than its opening pressure, this latter making it possible to control the pressure gradient (dp/dt) of the compression cycle. 37 diagrammatically shows a pressure sensor.

A pump 24 driven by an electric motor (not shown) introduces the compression fluid 25 at 0.7 MPa into the hydraulic unit. After compression to the maximum value desired, this returns to the tank 26 through the pipe 27 after opening of the valve 23 and through the pipes 27 and 17 through the piston 8 of the injection pump 5.

The apparatus likewise comprises the following members:
- a heat exchanger 28 for compression fluid:water
- a straining means 29 and a base valve 30
- a filter 31
- a leakage orifice 32 (in fact, in the original injector) connected to the return line 33 to the tank 26 permitting of an initial air bleed
- a regulator 34 for adjusting the level in the supply reservoir
- a greasing circuit 35, 36 if the compression fluid 25 is oil (the cam and the base of the piston of the injection pump then function in an oil bath).

The circuit carrying the heat bearing fluids comprises:
- two tanks 40F and 40C carrying heat bearing fluids 41F and 41C
- two circulating pumps 42F and 42C driven by electric motors 53, 54
- these pumps are connected through the connecting member 3 to water chambers 37 in cylinder head 1 by ducts 43F and 43C and a valve controlling the inlet 44 and the outlet 45 for circulating one or other fluid 41F or 41C in the cylinder head 1 being tested. The heat bearing fluid returns to the reservoirs by one of the two ducts 46F or 46C.

The reservoir 40F containing the fluid at ambient temperature is provided with a heat exchanger 47.

The reservoir 40C containing the hot fluid is provided with heating means such as the heating resistors 48 and temperature regulating means (not shown).

Placed on the circuits 43F or 43C are discharge valves calibrated to a security level of 50F and 50C.

The valves 44 and 45 are operated by electrically operated valves 51, 52 which are themselves controlled by a timing mechanism 49.

The cooling fluid(s) 41C, 41F may be chosen at will and may, for example, be oil, water to which anti-freeze products may or may not be added, etc.

On completion of the test, in the following way, the following are detected:
- on the one hand, by anomalies in the pressure cycles, for example a diminution in the upwards pressure gradient
- on the other, by a lowering of the level in the supply reservoir, a part of the fluid then passing into the circuits of heat bearing fluids.

The apparatus according to the invention makes it possible in limited times (particularly less than those called for in respect of engine test bench set-ups):
- for a given type of cylinder head, to define the alloy (or alloys) which are most suitable
- to develop new alloy compositions which are better adapted to the more and more severe requirements encountered in motor vehicle cylinder heads
- rapidly to test new types of cylinder head, and
- to draw up comparative mechanical fatigue schedules.

We claim:

1. A test bench for determining the mechanical fatigue resistance of cylinder heads having combustion chambers and water chambers, comprising:
   an intermediate connecting member adapted for fixing a cylinder head to be tested thereto;
   means for generating hydraulic pressure connected to the combustion chambers and comprising a monitoring chamber of adjustable volume for containing a hydraulic fluid, an injection pump comprising a piston and discharge system for pumping hydraulic fluid from said monitoring chamber to the combustion chambers, a supply pump for supplying hydraulic fluid to said monitoring chamber and said injection pump, and a bistable valve for regulating the pressure of fluid in said monitoring chamber and combustion chamber,
   said means for generating hydraulic pressure faithfully and reproducibly simulating a pressure cycle as a function of time in the combustion chamber, by operation of said injection pump, said monitoring chamber, said bistable valve and said discharge system; and
   means for circulating a heat bearing fluid in the water chambers comprising first and second circuits, said first circuit for circulating a heat-bearing fluid at ambient temperature and said second circuit for circulating a heat bearing fluid at a higher temperature than said first circuit, and means for regulating the circulation of fluids from said circuits.

2. A test bench according to claim 1, wherein the hydraulic fluid (25) is oil.

3. A test bench according to claim 1, wherein the volume of the monitoring chamber (19) is adjusted by a further piston (20).

4. A test bench according to claim 1, additionally comprising means to increase the pressure of the hydraulic fluid at a rate of 5 to 10 MPa/msec.

5. A test bench according to claim 1, additionally comprising means to establish a maximum relative pressure of hydraulic fluid between 2 and 20 MPa.

6. A test bench according to claim 3, 4 or 5, additionally comprising an adjustable cam controlling the stroke of said piston of the injection pump.

7. A test bench according to claim 1, 2, 3, 4 or 5, wherein the means for circulating a heat bearing fluid comprises two fluid reservoirs (40C, 40F), two circulating pumps (42C, 42F), two valves (44, 45) and inlet and return pipes (43F, 43C, 46F, 46C).

8. A bench according to claim 7, wherein the valves (44, 45) are operated by electrically operated valves (51, 52) which are themselves controlled by said means for regulating comprising a regulable timing mechanism.

9. A bench according to claim 8, wherein the timing mechanism imposes a cycle of greater than or equal to 3 mins.

10. A test bench according to claim 1, 2, 3, 4 or 5, wherein the heat bearing fluid is oil or water, optionally comprising an anti-freeze product.

11. A test bench according to claim 3, 4 or 5, wherein the discharge system comprises an axial bore in the piston of said injection pump, a plurality of radial channels through said piston connecting to said axial bore, a jacket surrounding said piston, and a lateral groove in said jacket communicating with said radial channels in a forward position of said piston.

* * * * *